US011299514B2

(12) United States Patent
Wang et al.

(10) Patent No.: US 11,299,514 B2
(45) Date of Patent: Apr. 12, 2022

(54) **ANTIMICROBIAL PEPTIDE AS-HEPC3$_{(48-56)}$ OF *ACANTHOPAGRUS SCHLEGELII* AND METHOD THEREOF**

(71) Applicant: Xiamen University, Fujian (CN)

(72) Inventors: Kejian Wang, Fujian (CN); Depeng Zhu, Fujian (CN); Hui Peng, Fujian (CN); Fangyi Chen, Fujian (CN); Huiyun Chen, Fujian (CN)

(73) Assignee: Xiamen University, Xiamen (CN)

( * ) Notice: Subject to any disclaimer, the term of this patent is extended or adjusted under 35 U.S.C. 154(b) by 0 days.

(21) Appl. No.: 17/373,042

(22) Filed: Jul. 12, 2021

(65) Prior Publication Data

US 2021/0340179 A1 Nov. 4, 2021

Related U.S. Application Data

(63) Continuation of application No. PCT/CN2020/093727, filed on Jun. 1, 2020.

(30) Foreign Application Priority Data

Oct. 9, 2019 (CN) ......................... 201910953094.7

(51) Int. Cl.

| | |
|---|---|
| ***C07K 7/06*** | (2006.01) |
| ***A61P 31/04*** | (2006.01) |
| ***A61K 38/00*** | (2006.01) |

(52) U.S. Cl.

CPC ................ *C07K 7/06* (2013.01); *A61P 31/04* (2018.01); *A61K 38/00* (2013.01)

(58) Field of Classification Search

CPC ......... C07K 7/06; C07K 14/461; A61P 31/04; A61K 38/00; Y02A 50/30

See application file for complete search history.

(56) References Cited

U.S. PATENT DOCUMENTS

2011/0183362 A1 7/2011 Lauth et al.

FOREIGN PATENT DOCUMENTS

| | | | |
|---|---|---|---|
| CN | 1641025 | A | 7/2005 |
| CN | 101063145 | A | 10/2007 |
| CN | 101906165 | A | 12/2010 |
| CN | 102517293 | A | 6/2012 |
| CN | 105732790 | A | 7/2016 |
| CN | 110170045 | A | 8/2019 |
| CN | 110776560 | A | 2/2020 |
| WO | 2014003538 | | 1/2014 |

OTHER PUBLICATIONS

Zhu et al. The Long-Term Effect of a Nine Amino-Acid Antimicrobial Peptide AS-hepc3(48-56) Against Psudomonas aeruginosa With No Detectable Resistance. Frontiers in Cellular and Infection Microbiology, Oct. 5, 2021, vol. 11, Article 752637, pp. 1-15. (Year: 2021).*

Yang M., et al., "Genomico and tissue-specific expression analysiss of of hepcidin-like from genes from black porgy (*Acanthopagrus schlegelii* B.)", Fish and Fish Shelllngey,vol. 23, No. 5, May 13, 2007 (May 13, 2007), http://mel2.xmu.edu.cn/member/upload_paper/2011926155231-YpUZaV.pdf, 12 pages.

International Search Report and English Translation cited in PCT/CN2020/093727 dated Sep. 4, 2020, 7 pages.

Written Opinion cited in PCT/CN2020/093727 dated Sep. 4, 2020, 4 pages.

Notice of Allowance and English translation cited in CN 201910953094.7 dated Dec. 15, 2020, 3 pages.

First Office Action and English translation cited in CN 201910953094.7 dated Oct. 22, 2020, 7 pages.

* cited by examiner

*Primary Examiner* — Marcela M Cordero Garcia

(74) *Attorney, Agent, or Firm* — Cooper Legal Group, LLC

(57) ABSTRACT

The present disclosure discloses an antimicrobial peptide AS-hepc3$_{(48-56)}$ of *Acanthopagrus schlegelii* and method thereof. A molecular formula of the antimicrobial peptide AS-hepc3$_{(48-56)}$ is $C_{48}H_{86}N_{24}O_{10}S_3$, and an amino acid sequence of the antimicrobial peptide AS-hepc3$_{(48-56)}$ is SEQ ID NO: 01.

5 Claims, 1 Drawing Sheet

Specification includes a Sequence Listing.

ANTIMICROBIAL PEPTIDE AS-HEPC3$_{(48-56)}$ OF *ACANTHOPAGRUS SCHLEGELII* AND METHOD THEREOF

RELATED APPLICATIONS

This application is a continuation of International patent application PCT/CN2020/093727, filed on Jun. 1, 2020, which claims priority to Chinese patent application 201910953094.7, filed on Oct. 9, 2019. International patent application PCT/CN2020/093727 and Chinese patent application 201910953094.7 are incorporated herein by reference.

REFERENCE TO AN ELECTRONIC SEQUENCE LISTING

The contents of the electronic sequence listing (SequenceListing.txt; Size: 464 bytes; and Date of Creation: Jul. 12, 2021) is herein incorporated by reference.

FIELD OF THE DISCLOSURE

The present disclosure relates to marine molecular biotechnology, and in particular relates to antimicrobial peptide AS-hepc3$_{(48-56)}$ of *Acanthopagrus schlegelii* and method thereof.

BACKGROUND OF THE DISCLOSURE

In 1928, British scientist Sir Alexander Fleming discovered the first antibiotic, penicillin. Since then, antibiotics have been continuously discovered, improved, and used in modern medicine. With the widespread use of antibiotics, antibiotic resistance has emerged and developed rapidly. The World Health Organization's (WHO's) 2014 report pointed out that antibiotic-resistant bacteria have spread globally, and we have entered the post-antibiotic era. At present, there are constant reports of antibiotic resistance worldwide, which has become an important issue that needs to be solved urgently. According to the WHO, at least 700,000 people die from drug-resistant diseases each year. If effective steps are not taken, this number will reach 10 million by 2050.

In the clinical isolation of drug-resistant bacteria, there are not only single drug-resistant bacteria, but also multi-drug resistant bacteria, extremely high drug-resistant bacteria, and completely drug-resistant bacteria, which brings huge challenges to clinical treatment. In 2017, WHO proposed to give priority to the development of new drugs to treat carbapenem-resistant *Pseudomonas aeruginosa*, carbapenem-resistant *Acinetobacter baumannii*, carbapenem-resistant and third-generation cephalosporin-resistant Enterobacteriaceae, Vancomycin-resistant enterococci, methicillin-resistant and vancomycin-resistant *Staphylococcus aureus*, and 12 other drug-resistant bacteria. It is currently believed that antibiotics have a single site of action, and bacteria can develop drug resistance through intrinsic drug-resistance, adaptive drug-resistance, and acquired drug-resistance. In contrast, antimicrobial peptides have diverse action sites and are not easy to develop drug resistance, making them one of the alternatives to antibiotics.

Antimicrobial peptides (AMPs), also known as host defense peptides, are mostly short peptides with positive charges, amphiphilic, and antimicrobial function. AMPs are widely present in animals, plants, microorganisms, and other organisms and are an important part of the innate immune system. AMPs have strong antimicrobial activity, have broad antimicrobial spectrum, and are not easy to induce bacteria to develop drug resistance. AMPs have good application prospects in production and application. At present, a variety of peptide drugs have been used in clinical treatment, providing new ideas and methods for reducing drug resistance.

BRIEF SUMMARY OF THE DISCLOSURE

In order to solve the deficiencies of the existing techniques, the present disclosure provides an antimicrobial peptide AS-hepc3$_{(48-56)}$ of *Acanthopagrus schlegelii* to solve the technical problems of the background.

In order to solve the aforementioned technical problems, a first technical solution of the present disclosure is as follows.

A molecular formula of the antimicrobial peptide AS-hepc3$_{(48-56)}$ is $C_{48}H_{86}N_{24}O_{10}S_3$, and an amino acid sequence of the antimicrobial peptide AS-hepc3$_{(48-56)}$ is SEQ ID NO: 01.

```
                                        (SEQ ID NO: 01)
Arg-Arg -Arg-Arg-Cys-Arg-Phe-Cys-Cys.
```

In an embodiment, a molecular weight of the antimicrobial peptide AS-hepc3$_{(48-56)}$ is 1255.567 Daltons.

In an embodiment, the antimicrobial peptide AS-hepc3$_{(48-56)}$ comprises 5 positively charged amino acid residues and 3 cysteine residues.

A second technical solution of the present disclosure is as follows.

A method for preparing an antimicrobial drug using the antimicrobial peptide AS-hepc3$_{(48-56)}$.

A third technical solution of the present disclosure is as follows.

An antimicrobial drug, an active ingredient of the antimicrobial drug comprises an antimicrobial peptide AS-hepc3$_{(48-56)}$ of *Acanthopagrus schlegelii*, and an amino acid sequence of the antimicrobial peptide AS-hepc3$_{(48-56)}$ is SEQ ID NO: 01.

In an embodiment, the active ingredient of the antimicrobial drug is the antimicrobial peptide AS-hepc3$_{(48-56)}$.

In an embodiment, the antimicrobial drug is configured to at least one of inhibit or kill at least one of *Pseudomonas aeruginosa, Staphylococcus aureus*, or *Escherichia coli.*

Compared with the existing techniques, the present disclosure has the following advantages.

1. The antimicrobial peptide AS-hepc3$_{(48_56)}$ of the present disclosure comprises 9 amino acids, the molecular formula is $C_{48}H_{86}N_{24}O_{10}S_3$, the molecular weight is 1255.567 Daltons, and the antimicrobial peptide AS-hepc3$_{(48-56)}$ comprises 5 positively charged amino acid residues and 3 cysteine residues. According to the charge of the amino acid residues, the isoelectric point of the antimicrobial peptide AS-hepc3$_{(48-56)}$ is predicted to be 11.40, the average coefficient of hydrophilicity is −1.356, and the antimicrobial peptide AS-hepc3$_{(48-56)}$ has good water solubility. The antimicrobial peptide AS-hepc3$_{(48-56)}$ is a positively charged cationic peptide with short length, is easy to synthesize, has broad antimicrobial spectrum, has high and stable antimicrobial activity, etc. and has good application prospects in drug research.

2. The antimicrobial peptide AS-hepc3$_{(48-56)}$ of the present disclosure has strong antimicrobial activity and is resistant to the development of drug resistance against clinically isolated drug-resistant *Pseudomonas aeruginosa*, drug-resistant *Staphylococcus aureus*, and drug-resistant *Escherichia coli*. In addition, the antimicrobial peptide AS-hepc3 $_{(48-56)}$ has no cytotoxicity to normal mouse liver cells AML12 (alpha mouse liver 12 cells) and human kidney epithelial cells 293T.

BRIEF DESCRIPTION OF THE DRAWINGS

FIGS. 2A and 2B illustrate cytotoxicity experimental result diagrams of antimicrobial peptide AS-hepc3$_{(48-56)}$ obtained by an MTS-PMS method, wherein FIG. 2A represents AML12 cells (alpha mouse liver 12 cells), FIG. 2B represents 293T cells, the abscissa represents an AS-hepc3$_{(48-56)}$ protein concentration (μM), and the ordinate represents a cell proliferation rate (%).

DETAILED DESCRIPTION OF THE EMBODIMENTS

Embodiment 1

Figure 1:
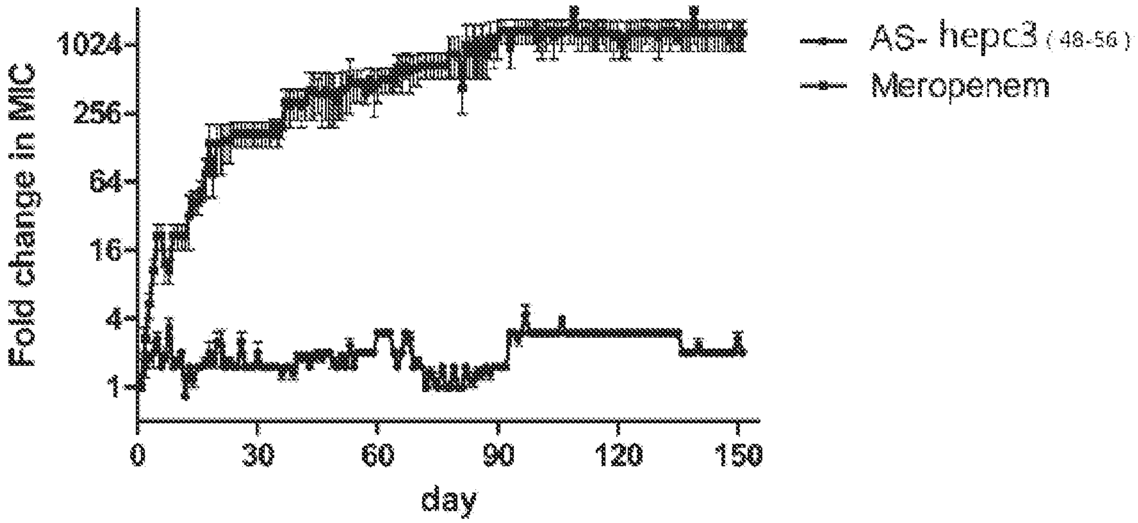
FIG. 1 illustrates a comparison of antimicrobial resistance of an antimicrobial peptide AS-hepc3$_{(48-56)}$ of *Acanthopagrus schlegelii* and antibiotic meropenem against *Pseudomonas aeruginosa* PAO1, wherein the abscissa represents time (days), and the ordinate represents a ratio of change of a minimum inhibition concentration (MIC) and an initial antimicrobial concentration.

An amino acid sequence of an antimicrobial peptide AS-hepc3$_{(48-56)}$ of *Acanthopagrus schlegelii* of this embodiment is as follows.

```
                                        (SEQ ID NO: 01)
Arg-Arg-Arg-Arg-Cys-Arg-Phe-Cys-Cys
```

In this embodiment, the antimicrobial peptide AS-hepc3$_{(48-56)}$ was synthesized by GL Biochemical (Shanghai) Co., Ltd. by a solid-phase synthesis method, and a purity of the antimicrobial peptide AS-hepc3$_{(48-56)}$ was more than 95%. Detection information comprising polypeptide molecular weight, HPLC (high-performance liquid chromatograph), etc. were provided, and related physicochemical parameters are shown in Table 1.

TABLE 1

Physicochemical parameters of antimicrobial peptide AS-hepc3$_{(48-56)}$

| Physicochemical parameter | AS-hepc3$_{(48-56)}$ |
|---|---|
| Number of amino acid residues | 9 |
| Molecular weight | 1255.567 Da (Daltons) |
| Molecular formula | $C_{48}H_{86}N_{24}O_{10}S_3$ |
| Isoelectric point | 11.40 |
| Net charge | +5 |
| Hydrophobicity | 44% |
| Total average hydrophilicity | −1.356 |
| Protein binding potential energy | 2.2 kcal/mol |
| Molar extinction coefficient | 187.5 |

Referring to Table 1, the antimicrobial peptide AS-hepc3$_{(48-56)}$ of this embodiment has a small molecular weight, good stability, and high water solubility, and the antimicrobial peptide AS-hepc3$_{(48-56)}$ is a positively charged cationic polypeptide.

Embodiment 2: Verification of Minimum Inhibition Concentration (MIC) and Minimum Bactericidal Concentration (MBC)

1. Strains were as follows: *Pseudomonas aeruginosa* PAO1, drug-resistant clinical *Pseudomonas aeruginosa* isolates QZ19121, QZ19122, QZ19123, QZ19124, and QZ19125, drug-resistant clinical *Acinetobacter baumannii* isolates QZ18050 and QZ18055, clinical isolation of resistant *Staphylococcus aureus* QZ18090 and QZ18091, drug-resistant clinical *Klebsiella pneumoniae* isolate QZ18106, and drug-resistant clinical *Escherichia coli* isolates QZ18109 and QZ18110. *Pseudomonas aeruginosa* PAO1 was purchased from the China General Microbiological Culture Collection Center, Institute of Microbiology, Chinese Academy of Sciences, and the clinical isolates were from the Laboratory of Second Affiliated Hospital of Fujian Medical University.

2. A detailed method is as follows.

(1) Preserved strains were streaked on MH plates (Mueller-Hinton agar plates) and were cultured at 37° C. overnight;

(2) A single clone was screened and was cultured in a MH liquid medium (Mueller-Hinton agar liquid medium) at 37° C. and 200 rpm (revolutions per minute) to a logarithmic stage;

(3) The strains were collected at 5000 g (i.e., a 5000 g centrifugal force) for 2 minutes, the strains were resuspended with a 10 mM (mmol/L) sodium phosphate buffer (pH=7.4), and the strains were finally diluted with the MH liquid medium to enable a final concentration of the strains to be 5×10$^5$ cfu/mL;

(4) Synthesized powder of the antimicrobial peptide AS-hepc3$_{(48-56)}$ was dissolved in sterile Milli-Q water, and a peptide concentration (i.e., a concentration of the antimicrobial peptide AS-hepc3$_{(48-56)}$) was diluted to 2 μM, 4 μM, 8 μM, 16 μM, 32 μM, or 64 μM in double ratios; and (5) On a polypropylene sterile 96-well culture plate, each test strain was arranged into a blank control group, a negative control group, and a test group, and three parallel groups of each test group were as follows:

a) Blank control group: 50 μL of test peptide sample (i.e., the antimicrobial peptide AS-hepc3$_{(48-56)}$) and 50 μL of medium (i.e., the Mueller-Hinton agar liquid medium);
b) Negative control group: 50 μL of sterile Milli-Q water and 50 μL of strain suspension; and
c) Test group: 50 μL of test peptide sample and 50 μL of the strain suspension.

The polypropylene sterile 96-well culture plate was placed in a 37° C. incubator for 18-24 hours, and MIC results in the test group were observed. After the test group was pipetted and mixed, an appropriate amount of the strain was drawn and spread on the MH plate and was cultured at 37° C. overnight, and MBC results were observed.

3. The MIC and MBC results of the antimicrobial peptide AS-hepc3$_{(48-56)}$ are shown in Table 2.

TABLE 2

Antimicrobial activity of the antimicrobial peptide AS-hepc3$_{(48-56)}$

| Strain | Microorganism | NO. | MIC | MBC |
|---|---|---|---|---|
| *Pseudomonas aeruginosa* PAO1 | *P. aeruginosa* | CGMCC: 1.12483 | 4-8 | 8 |
| *Pseudomonas aeruginosa* | *P. aeruginosa* | QZ19121 | 4-8 | 16 |
| *Pseudomonas aeruginosa* | *P. aeruginosa* | QZ19122 | 4-8 | 16 |
| *Pseudomonas aeruginosa* | *P. aeruginosa* | QZ19123 | 4-8 | 16 |
| *Pseudomonas aeruginosa* | *P. aeruginosa* | QZ19124 | 4-8 | 16 |
| *Pseudomonas aeruginosa* | *P. aeruginosa* | QZ19125 | 8-16 | 16 |
| *Acinetobacter baumannii* | *A. baumannii* | QZ18050 | >32 | >32 |
| *Acinetobacter baumannii* | *A. baumannii* | QZ18055 | >32 | >32 |
| *Staphylococcus aureus* | *S. aureus* | QZ18090 | 4-8 | 8 |
| *Staphylococcus aureus* | *S. aureus* | QZ18091 | 4-8 | 8 |
| *Klebsiella pneumoniae* | *K. pneumoniae* | QZ18106 | >32 | >32 |

TABLE 2-continued

Antimicrobial activity of the antimicrobial peptide AS-hepc3$_{(48-56)}$

| Strain | Microorganism | NO. | MIC | MBC |
|---|---|---|---|---|
| *Escherichia coli* | *E. coli* | QZ18109 | 4-8 | 16 |
| *Escherichia coli* | *E. coli* | QZ18110 | 4-8 | 8 |

Annotations: MIC: minimum inhibitory concentration (μM), which is represented by a-b; a is a maximum peptide concentration at which a growth of the strain can be observed by naked eyes, and b is a minimum peptide concentration at which no growth of the strain can be observed by the naked eyes. MBC: Minimum bactericidal concentration (μM), which is a concentration that kills 99.9% of microbes.

Embodiment 3: Comparative Experiments of Drug Resistance

1. Comparison of the antimicrobial peptide AS-hepc3$_{(48-56)}$ and antibiotic meropenem against *Pseudomonas aeruginosa* PAO1. *Pseudomonas Aeruginosa* PAO1 was purchased from the China General Microbiological Culture Collection Center, Institute of Microbiology, Chinese Academy of Sciences.

A detailed method is as follows:

(1) Preserved *Pseudomonas aeruginosa* PAO1 was streaked on MH plates and was cultured at 37° C. overnight;

(2) A single clone was screened and was cultured in MH liquid medium at 37° C. and 200 rpm to a logarithmic stage;

(3) The strain was corrected at 5000 g for 2 minutes, the strain was resuspended in 10 mM sodium phosphate buffer (pH=7.4), and the strain was finally diluted with a mixture of the 10 mM sodium phosphate buffer and the MH liquid medium to enable a final concentration of the stain to be $5\times10^5$ cfu/mL;

(4) Synthesized powder of the antimicrobial peptide AS-hepc3$_{(48-56)}$ was dissolved in sterile Milli-Q water, and a peptide concentration was diluted to 8 μM, 12 μM, 16 μM, 24 μM, 32 μM, 48 μM, 64 μM, or 96 μM in double ratios;

(5) Antibiotic meropenem powder was dissolved in sterile Milli-Q water to configure a 5 mg/mL reserved solution, filtered by a 0.22 μm filter membrane, and diluted to different work concentrations being 0.0625 μg/mL, 0.125 μg/mL, 0.25 μg/mL, 0.5 μg/mL, 1 μg/mL, 2 μg/mL, 4 μg/mL, 8 μg/mL, 16 μg/mL, 32 μg/mL, 48 μg/mL, 64 μg/mL, 96 μg/mL, 128 μg/mL, 192 μg/mL, 256 μg/mL, or 512 μg/mL; and (6) On a 96-well cell culture plate, each test strain was arranged into a blank control group, a negative control group, and a test group, and three parallel groups of each test group were as follows:

a) Blank control group: 50 μL of test peptide sample and 50 μL of medium;

b) Negative control group: 50 μL of sterile Milli-Q water and 50 μL of strain suspension; and c) Test group: 50 μL of the test peptide sample and 50 μL of the strain suspension.

The 96-well cell culture plate was placed in a 37° C. incubator and was cultured for 18-24 hours, and MIC results in the test group were observed. The strain having the maximum peptide concentration at which the growth of the strain could be observed was repeatedly diluted thousand-fold, and 50 μL was repeatedly taken for a next generation of antimicrobial experiments for 150 generations.

3. The results are shown in FIG. 1. When the antibiotic meropenem was used to act on *Pseudomonas aeruginosa* PAO1, an anti-*Pseudomonas aeruginosa* MIC value of the antibiotic meropenem was increased to 4 times an initial MIC value after 3 days. The anti-*Pseudomonas aeruginosa* MIC value was increased to 16 times the initial MIC value and was increased continually after 10 days of continuous use. The anti-*Pseudomonas aeruginosa* MIC value increased 1024 times after 90 days of use, which indicates that *Pseudomonas aeruginosa* has high drug resistance to the antibiotic meropenem. However, when the antimicrobial peptide AS-hepc3$_{(48-56)}$ was used to act on *Pseudomonas aeruginosa* PAO1, the anti-*Pseudomonas aeruginosa* MIC value of the antimicrobial peptide AS-hepc3$_{(48-56)}$ was only twice of the initial MIC value after 150 days of continuous use. There was no significant change, which indicates that *Pseudomonas aeruginosa* has no obvious drug-resistant effect on the antimicrobial peptide AS-hepc3$_{(48-56)}$.

Embodiment 4: Detection of Cytotoxicity

1. Mouse hepatocytes (AML12) (mouse liver cells) and human kidney epithelial cells (293T) were selected to detect a cytotoxicity of the antimicrobial peptide AS-hepc3$_{(48-56)}$.

2. A detailed method is as follows.

(6) Well-grown mouse hepatocytes (AML12) and human kidney epithelial cells (293T) were collected, a cell concentration was adjusted to $10^3$-$10^4$ cells/mL, the cells were evenly blown, and 100 μL of strain suspension was placed in each well of a 96-well cell culture plate and was static cultured at a condition of 37° C. and 0.5% $CO_2$. More than 50% of the strains were adhered to a wall.

(7) The medium is carefully sucked out, a corresponding medium comprising different concentrations (0 μM, 40 μM, or 80 μM) was added and was static cultured for 24 hours at a condition of 37° C. and 0.5% $CO_2$.

(8) After 20 μL of MTS-PMS solution was added and was incubated for 3 hours in the dark, an $OD_{492}$ value (optical density reading at 492 nm wavelength) was detected by a microplate reader to evaluate the cytotoxicity of the antimicrobial peptide AS-hepc3$_{(48-56)}$.

Figure 2A:
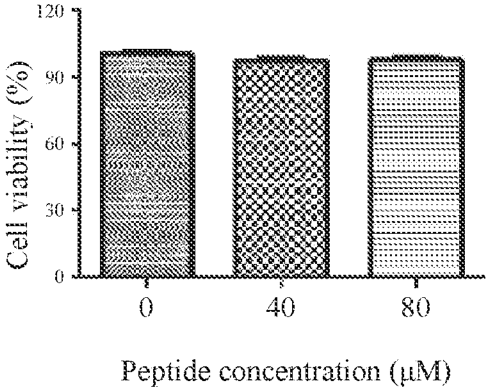
Figure 2B:
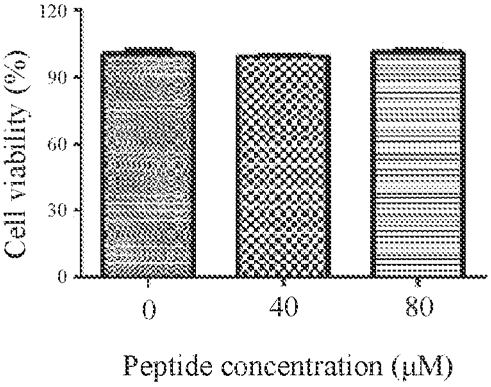

3. The results are shown in FIG. 2.

In a condition of 5 times and 10 times MIC (40 μM and 80 μM), after the antimicrobial peptide AS-hepc3$_{(48-56)}$ and AML12 cells (FIG. 2A) and 293T cells (FIG. 2B) were co-incubated for 24 hours, a cell survival rate of the test group was more than 95% compared with the control group, which indicated that the antimicrobial peptide AS-hepc3$_{(48-56)}$ has no cytotoxicity.

The aforementioned embodiments are merely some embodiments of the present disclosure, and the scope of the disclosure is not limited thereto. Thus, it is intended that the present disclosure cover any modifications and variations of the presently presented embodiments provided they are made without departing from the appended claims and the specification of the present disclosure.

What is claimed is:

1. An antimicrobial peptide consisting of SEQ ID NO: 1.

2. The antimicrobial peptide according to claim 1, wherein a molecular weight of the antimicrobial peptide is 1255.567 Daltons.

3. A method for preparing an antimicrobial drug, comprising:

dissolving the antimicrobial peptide according to claim 1 in a solution.

4. An antimicrobial drug, comprising:

an antimicrobial peptide consisting of SEQ ID NO: 1.

5. A method for preparing an antimicrobial drug, comprising:

dissolving the antimicrobial peptide according to claim 2 in a solution.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Arg Arg Arg Arg Cys Arg Phe Cys Cys
1               5
```